United States Patent [19]

Cipolla

[11] Patent Number: 5,458,628
[45] Date of Patent: Oct. 17, 1995

[54] THERAPEUTIC HEATING PADS AND COVERS THEREFOR

[76] Inventor: Eloisa Cipolla, 321 Nolana Loop, McAllen, Tex. 78504

[21] Appl. No.: 203,043

[22] Filed: Feb. 28, 1994

[51] Int. Cl.[6] ............................................. A61F 7/00
[52] U.S. Cl. ........................... 607/112; 607/114; 165/46
[58] Field of Search .................. 607/108–112, 114; 383/901; 62/530; 165/46

[56] References Cited

U.S. PATENT DOCUMENTS

| | | |
|---|---|---|
| 3,587,578 | 6/1971 | Walker . |
| 3,815,610 | 6/1974 | Winther . |
| 3,889,684 | 6/1975 | LeBold . |
| 4,252,119 | 2/1981 | Coates . |
| 4,381,025 | 4/1983 | Schooley . |
| 4,539,982 | 9/1985 | Bailly . |
| 4,676,247 | 7/1987 | Van Cleve ............................ 607/112 |
| 4,753,241 | 6/1988 | Brannigan et al. . |
| 4,805,619 | 2/1989 | Swearingen . |
| 4,805,620 | 2/1989 | Meistrell ............................... 607/112 |
| 4,913,957 | 4/1990 | Strack . |
| 4,961,418 | 10/1990 | McLaurin-Smith . |
| 4,972,832 | 11/1990 | Trapini et al. ......................... 607/108 |
| 5,062,414 | 11/1991 | Grim ...................................... 607/108 |
| 5,129,391 | 7/1992 | Brodsky et al. ....................... 607/114 |
| 5,133,348 | 7/1992 | Mayn . |
| 5,215,080 | 6/1993 | Thomas et al. ........................ 607/112 |
| 5,274,865 | 1/1994 | Takehashi ............................. 607/109 |

*Primary Examiner*—Lee S. Cohen
*Assistant Examiner*—Robert L. Nasser, Jr.
*Attorney, Agent, or Firm*—Richard C. Litman

[57] ABSTRACT

Therapeutic heating pads and covers serve to preclude direct contact between a patient and any heating pad or towels applied. The covers thus serve to lessen soiling or contamination of the towels or pads. The pad cover material is non-absorbent and moisture or liquid impervious, providing for ease of cleanup and sanitation. The pads and covers may be provided in a variety of shapes and sizes in order to conform better to specific areas of the anatomy and include securing straps enabling the pad covers to be secured to the desired area of the patient.

10 Claims, 4 Drawing Sheets

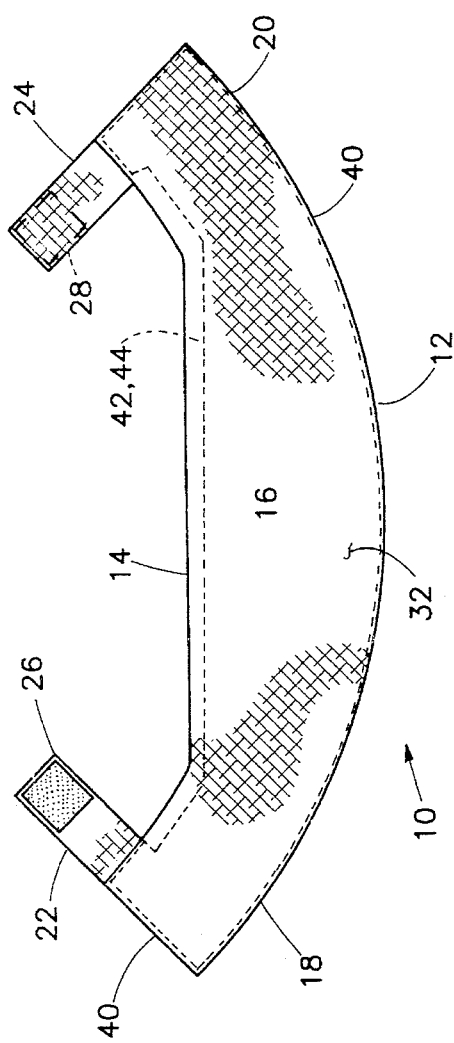
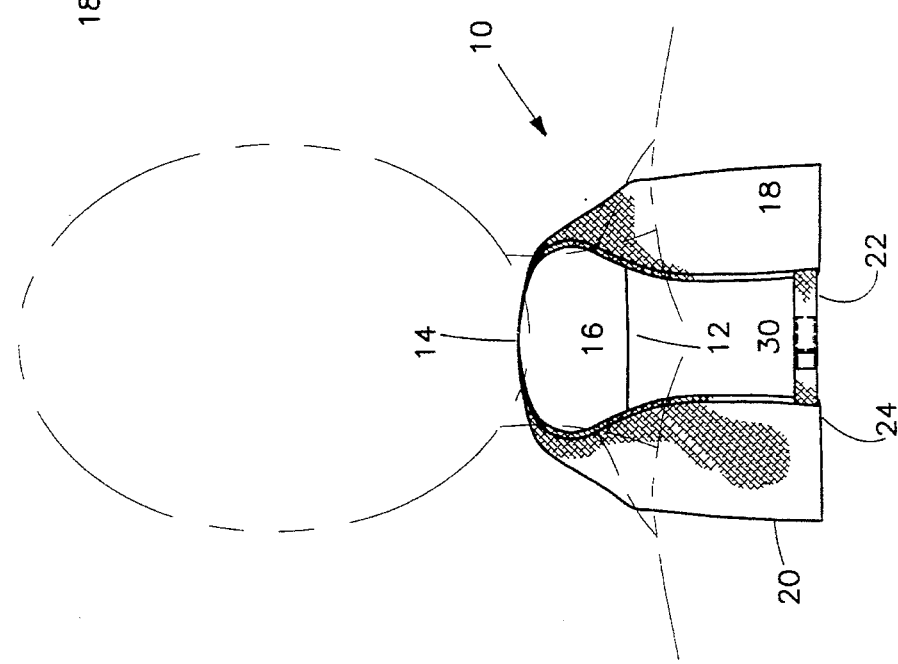
Fig. 1
Fig. 2

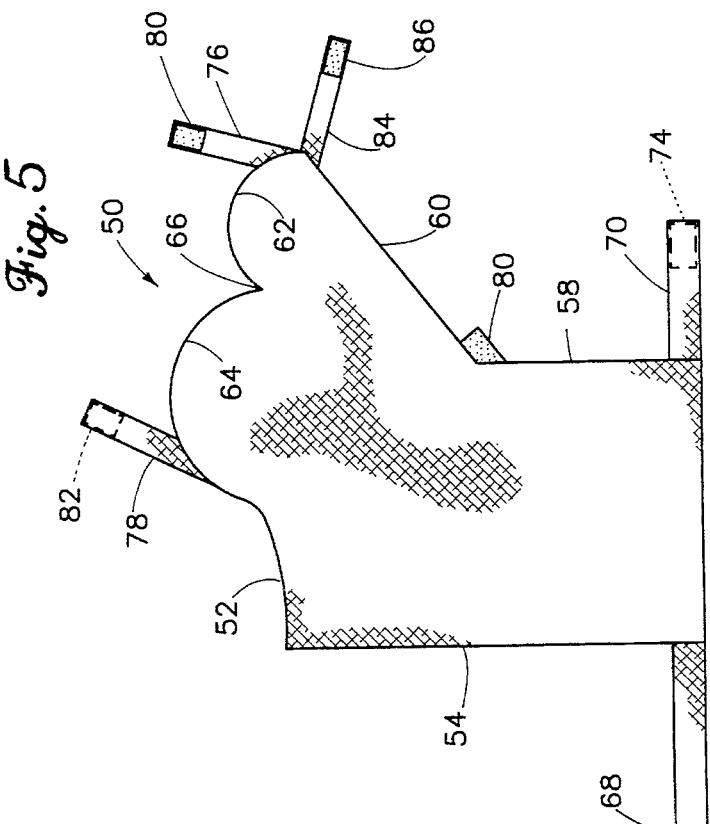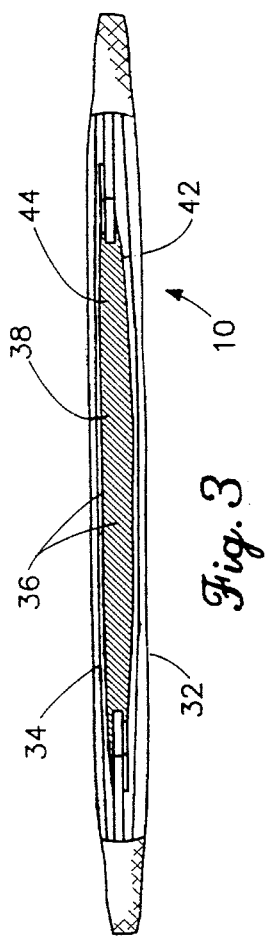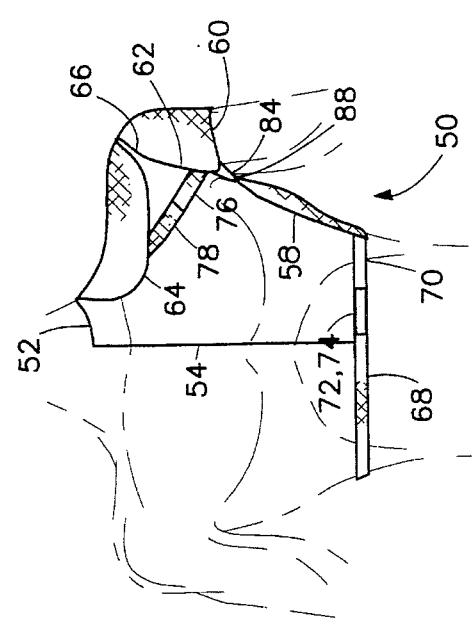

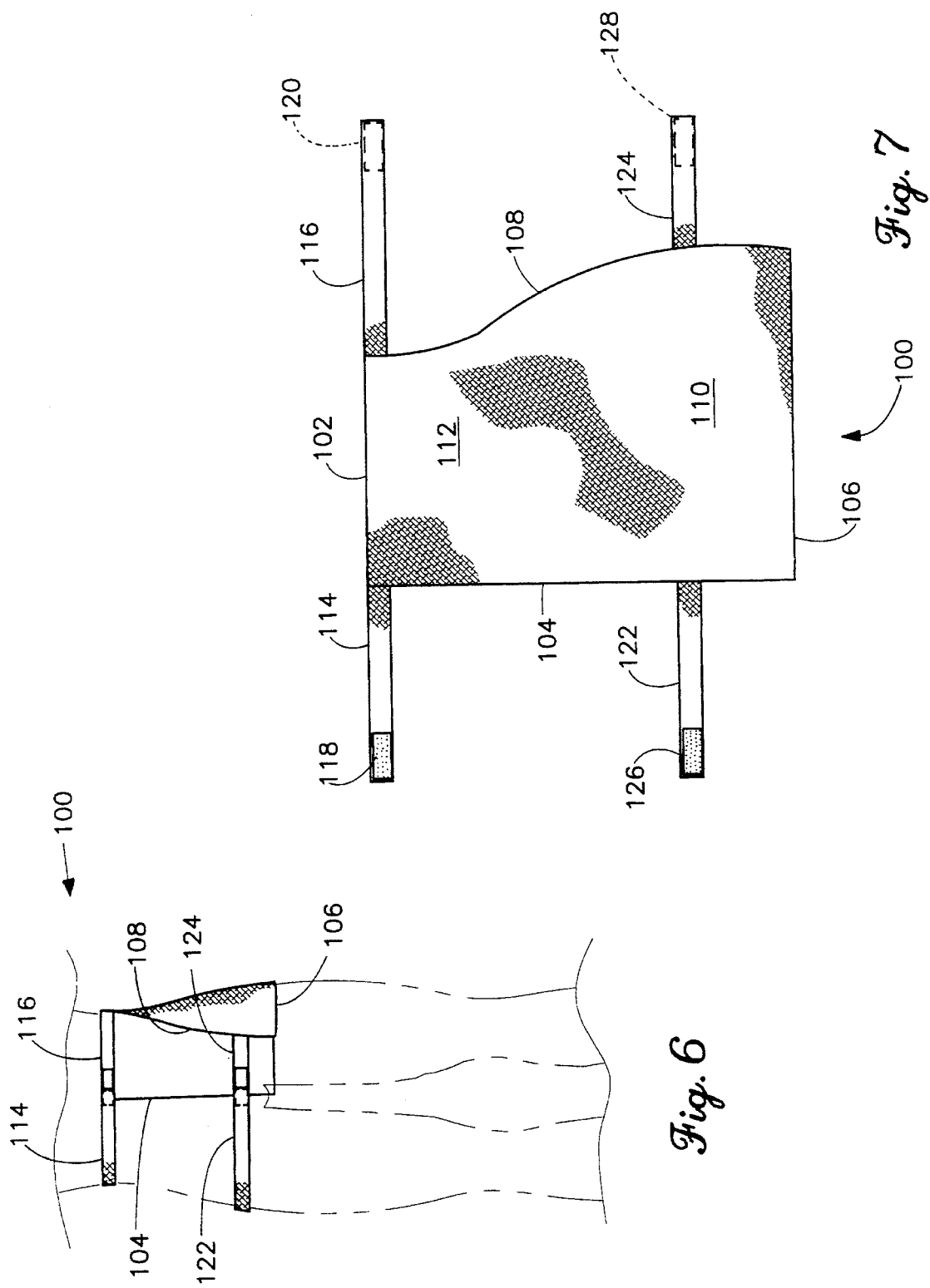

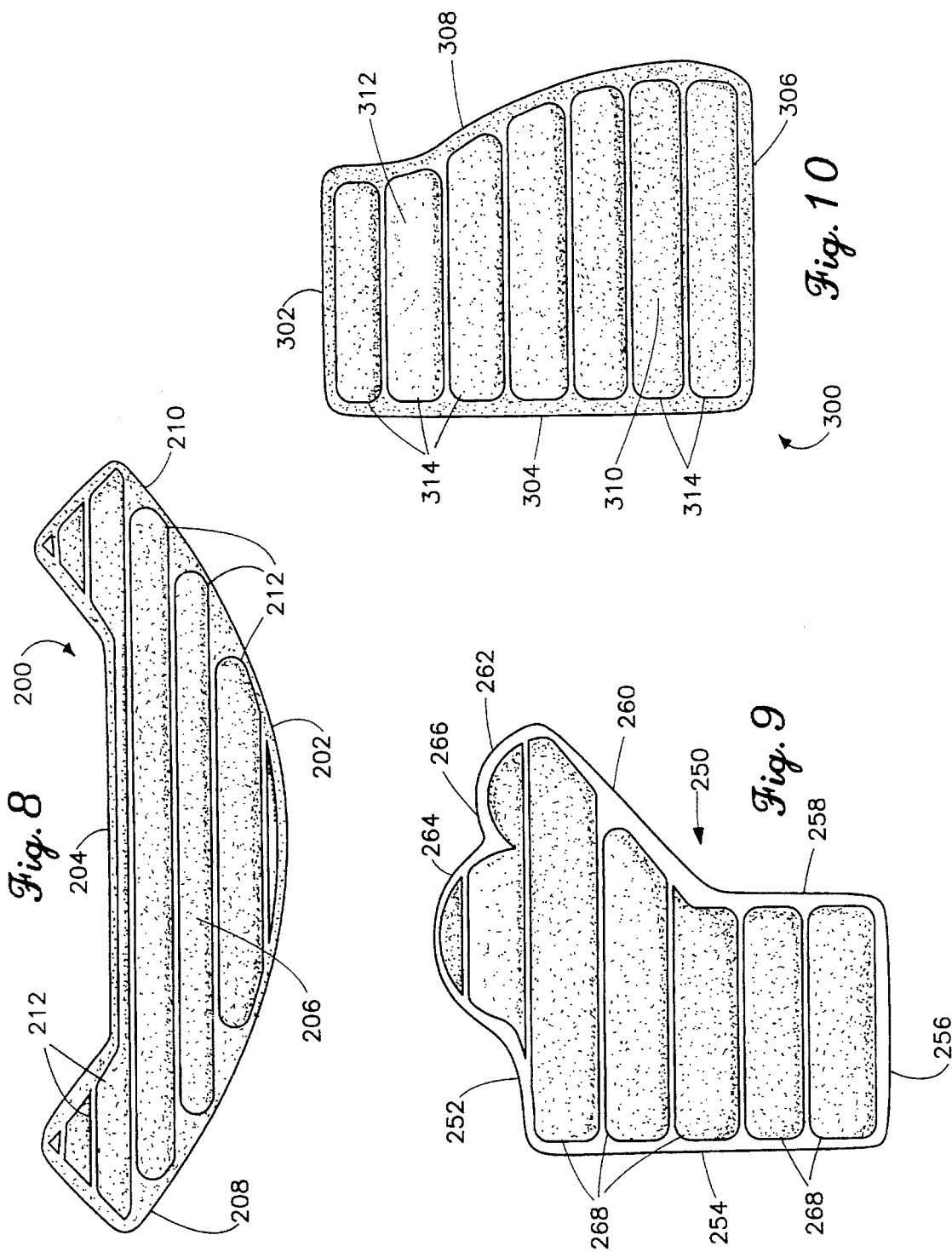

THERAPEUTIC HEATING PADS AND COVERS THEREFOR

FIELD OF THE INVENTION

The present invention relates generally to therapeutic heating pads and covers for use in the medical field, and more specifically to pads and non-absorbent, moistureproof covers for such pads, which pads and covers are specially formed to provide a close fit about various portions of a patient's anatomy for the treatment of tendinitis, bursitis, or other similar muscular and joint problems.

BACKGROUND OF THE INVENTION

Hot/moist packs, also known as hydrocollator packs, have been used in the treatment of muscular and joint problems for many years, and the benefits of either dry or moist heat in the treatment of such problems has been known for quite some time. In the past, such hot packs were encased entirely in towels with no other exterior protective cover. Generally the packs tend to cool in a relatively short time due to evaporation through the towels and other effects, which requires their reheating and rehumidifying for continued treatment. In any case, those towels become soiled from contact with a patient's body or by the hot pad chemicals. They also become wet as they absorb the water from the hot pad. These factors then require the towels to be laundered after use on each individual patient as they could become mixed with and/or contaminate other towels.

In response, heating pad covers were developed in order to eliminate the use of so many towels to cover the hot pads. However, these earlier covers are generally formed of a terry cloth type material, and tend to absorb the humidity and contaminates from either the patient the pad, and/or from any treatment placed on the patients themselves, and/or the Gels which seep from the hot pads. No disclosure is made in present patents of the means to prevent contamination of the covers as they absorb the water and seeping gel from the hot pads that gets captured between the different layers of the cover. The terry cloth material of the present covers has no other means of cleaning than frequent laundering to prevent contamination and foul smell, unlike the present invention. In addition, neither the pads nor covers currently known to be in use in the field provide specific shapes for the treatment of specific areas of the body, and none are formed of a non-absorbent, moisture repellent material that protects them from contamination from the pad material (seeping gel), patient factors, and from heat and water retention. Due to the moisture absorbency of such terry cloth cover material, the heat of a moist hot pack dissipates relatively rapidly due to evaporation, which requires more frequent heating of the pack(s).

The need arises for therapeutic heating pads and covers therefor which are capable of completely containing the pads therein, which covers are formed of a non-absorbent and moisture repellent material in order to provide for ease of cleanup of the pad covers and for heat and water retention of a pad contained therein. The pads and covers must be formed in specific shapes and sizes in order to conform properly to areas of the body commonly requiring such treatment, and the covers must further include specific fastening or attachment means providing for securing to such specific areas of the body.

DESCRIPTION OF THE PRIOR ART

U.S. Pat. No. 3,587,578 issued to Jack M. Walker on Jun. 28, 1971, discloses a Pack For Applying Therapeutic Moist Heat. The device includes a moisture impervious sheet on the outer side, with an absorbent fabric material sandwiched to the inner surface and a moisture absorbent material (e.g., aluminum silicate or bentonite gel) captured between the two layers. This absorbent material obtains the heat from the water in which it is contained and delivers the heat to the treated area. The amount of heat and water lost depends greatly on the cover the pad is placed in.

U.S. Pat. No. 3,815,610 issued to Thorkil Winther on Jun. 11, 1974, discloses a Body-Attachable Steam Pack Cover for the containment of a steam pack. The device does not so much provide a pocket for the containment of the heated material, as it rather folds over or about the heated material. A continuous strap extends across the device to provide for the complete surrounding of the patient's neck and closure about the throat, unlike the present invention.

U.S. Pat. No. 3.889,684 issued to Steve Lebold on Jun. 17, 1975, discloses a Hot And Cold Pack resembling a more complex, multilayered version of the Winther device discussed above. A moisture absorbent material is disclosed which is placed within a moistureproof pack, which pack is then folded within a flat, planar cover and then finally secured to the patient. While the disclosure states that the device may be formed to conform to various areas of the body, the only specific disclosed shapes completely encircle various portions of the body, unlike the present invention.

U.S. Pat. No. 4,252,119 issued to John T. Coates on Feb. 24, 1981, discloses a Pack For Moist Patient Therapy having a sterile, single use pad enclosed in a sealed, disposable liquid impervious envelope. The envelope provides a sterile environment for the disposable pad therein, but all elements are discarded after a single use, unlike the present invention.

U.S. Pat. No. 4,381,025 issued to Constance E. Schooley on Apr. 26, 1983, discloses a Cover For Instant Hot Or Cold Pack. The cover is impervious to liquids, but makes no provision for securing to a patient's body. The only closure means for the pack are two cooperating tabs, which provide only discontinuous closure and an imperfect seal.

U.S. Pat. No. 4,539,982 issued to Richard L. Bailly on Sep. 10, 1985, discloses an Odor Absorbing Wrap comprising a tape having an odor absorbing chemical therein. The tape is to be wrapped around a patient's body prior to installing a cast on that area. It does not provide a therapeutic pad or cover.

U.S. Pat. No. 4,753,241 issued to Patrick J. Brannigan et al. on Jun. 28, 1988, discloses a Method Of Forming And Using A Therapeutic Device. The device is similar to the Walker device discussed above.

U.S. Pat. No. 4,805,619 issued to David W. Swearingen on Feb. 21, 1989, discloses a Therapeutic Cooling Scarf, Wrap Or Collar comprising a hollow tubular member having a liquid impervious inner liner. Two separate securing means are disclosed, to hold the ends of the tube together and to secure the device about the user.

U.S. Pat. No. 4,805,620 issued to William R. Meistrell on Feb. 21, 1989, discloses an Adjustable, Wrappable, Stretchable Wrap Sheet having a central opening and plural extensions. The opening provides for the securing of a hot or cold pack therethrough and the plural extensions are securable about a person's arm or leg, and the resulting space between the interconnected extensions allows the limb to flex. No envelope is provided for the containment of a heat or cold pack, nor is the device securable about other parts of the anatomy.

U.S. Pat. No. 4,913,957 issued to David C. Strack et al. on Apr. 3, 1990 discloses a Thermal Retaining Fabric Laminate including multiple layers serving essentially the same purpose as a hot or cold pack and an impervious overlay.

U.S. Pat. No. 4,961,418 issued to Mark McLaurin-Smith on Oct. 9, 1990. discloses Heat Retaining Fabric And Physical Therapy Appliances. The device is bonded together as a single sheet of material, with no means provided to form a pocket therein to hold heated pads adjacent the body. In fact, the material specifically provides for air circulation between the material and the underlying skin, which precludes functioning as a cover holding a moist heated pad against the body.

Finally, U.S. Pat. No. 5,133,348 issued to Alice M. Mayn on Jul. 28, 1992, discloses a Contoured Cooling Pack having a liquid impervious layer (polyethylene) incorporated therein.

None of the above noted patents, taken either singly or in combination, are seen to disclose the specific arrangement of concepts disclosed by the present invention.

SUMMARY OF THE INVENTION

By the present invention, improved therapeutic pads and covers therefor are disclosed.

Accordingly, one of the objects of the present invention is to provide improved therapeutic heating pad covers which are capable of containing moisturized heating pads therein, and controlling the transmittal of heat in the pads through the cover to the patient.

Another of the objects of the present invention is to provide improved therapeutic heating pad covers which are non-absorbent, so as to preclude being permeated with odors and/or stains from the pad's gel or contamination from the patient, since the cover may be cleaned with an antiseptic solution at the patient's side, thus avoiding contamination between users.

Yet another of the objects of the present invention is to provide improved therapeutic heating pad covers which provide protection to the pads contained therein from losing a great deal of heat and humidity, therefore shortening the reheating time.

Still another of the objects of the present invention is to provide improved therapeutic heating pad covers which include at least one openable and sealable edge, providing access to the interior of the cover for insertion and removal of pads therefrom.

A further object of the present invention is to provide improved therapeutic heating pads and covers which are shaped to conform to areas and joints of the human body which are commonly afflicted with muscle or joint problems requiring such therapeutic treatment.

An additional object of the present invention is to provide improved therapeutic heating pads and covers which include means for securing the pads to specific areas of the human body.

A final object of the present invention is to provide improved therapeutic heating pads and covers therefor for the purposes described which are more hygienic, inexpensive, dependable and fully effective in accomplishing their intended purpose.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

FIG. 1 is a front perspective view of one embodiment of the therapeutic heating pad cover of the present invention, showing it as it would fit and conform about a person's neck and further showing the securing means used.

FIG. 2 is a plan view of the pad cover of FIG. 1 laid out flat, and showing various construction details.

FIG. 3 is a top view of the pad cover of FIGS. 1 and 2, showing the interior thereof and closure means.

FIG. 4 is a front view of a second embodiment of the pad cover of the present invention, showing its fit about a person's shoulder and upper back, and the securing means therefor.

FIG. 5 is a plan view of the pad cover of FIG. 4 laid out flat and showing its construction details.

FIG. 6 is a front view of a third embodiment of the pad cover of the present invention, showing its fit about a person's waist and hip and securing means.

FIG. 7 is a plan view of the pad cover of FIG. 6 laid out flat and showing its details.

FIG. 8 is a plan view of a cervical therapeutic heating pad configured to fit within the pad cover shown in FIGS. 1 through 3.

FIG. 9 is a plan view of a shoulder/thoracic heating pad configured to fit within the pad cover shown in FIGS. 4 and 5.

FIG. 10 is a plan view of a lumbo-sacral waist and hip heating pad configured to fit within the pad cover shown in FIGS. 6 and 7.

Similar reference characters denote corresponding features consistently throughout the several figures of the attached drawings.

DETAILED DESCRIPTION OF THE PREFERRED EMBODIMENTS

Referring now particularly to FIG. 1 of the drawings, a first embodiment of the present invention will be seen to relate to a cervical heating pad cover 10 formed and shaped to fit about and conform particularly to the back and sides of the neck of a patient. Cover 10 is preferably formed of at least two layers of a moisture or liquid repellent material, in order that moisture and seeping gel will be retained therein, and the material is also non-absorbent in order to provide ease of cleanup and good hygiene. Several models were constructed before a Nylon (TM) fabric material was used, which has produced satisfactory results. The Nylon is also capable of withstanding the relatively high heat produced by the hot pad after it has been properly heated in the hydrocollator tank. For better heat retention and uniform release of the heat of a pad contained therein, the Nylon is preferably reflectively coated, e.g., aluminized.

Various embodiments of the present invention have been developed in order to provide effective treatment to areas of the body commonly afflicted with muscle and joint injuries or problems. In each case, the pad covers are constructed of two layers of material (preferably a Nylon synthetic fabric, as noted above) that enclose an aluminized fabric and two other layers of insulation material to regulate the heat transmission. They are stitched or otherwise secured together and completely contained within an outer layer of Nylon. These covers are made as an open book, so as the hot pad is placed within, it will close and secure the pad within. It is secured on the opposite side of the permanently stitched side with hook and loop closure, and on the other two sides may be closed by suitable means. (Specific pads configured to cooperate with the covers shown in FIGS. 1 through 7, are shown in FIGS. 8 through 10 and are discussed following the discussion of the various cover configurations.) At least one of the open sides is then closed by suitable means, e.g., hook and loop material, to form a secure fit for the heating pad and its cover on the patient for optimal therapeutic results.

Pad cover 10 of FIGS. 1 through 3 is specifically formed to fit closely about the back and sides of the neck area of a patient, and extend or drape downward over each side of the neck. Typical injuries to the muscular structure of the neck and joints of the cervical vertebrae will be covered by the pad cover 10 of FIGS. 1 through 3. It will be noted in FIG. 2 that the cover 10 includes a lower edge 12 having a convex curvature, in order to drape downward across the lower cervical vertebrae to a better extent, and yet has a straight upper edge 14 to provide higher coverage across the back of the neck, about the occipital ridge from the mastoid process on the left to the same on the right. The resulting wider central portion 16 provides greater area for more effective treatment.

Left and right frontal neck extensions 18 and 20 extend respectively from the left and right ends of the central area 16, to provide a frontal drape for the pad 10 of FIG. 1. Extensions 18 and 20 each include first and second securing straps 22 and 24, respectively, extending inwardly therefrom and toward one another, thus providing marina securing means at the distal ends thereof (e.g., cooperating first and second hook and loop fastening material portions 26 and 28, respectively) when the pad 10 is draped about a patient's neck. It will be noted that the extensions 18 and 20 do not overlap or contact one another at the front, but rather a space 30 is left when the pad cover 10 is properly fitted, in order to provide greater comfort and freedom to the patient while still covering the muscle groups involved in the treatment.

FIG. 3 provides a top view of the pad cover 10, showing first layer 32 of 100% of liquid impervious material, e.g., nylon and second layer 34 of and after "of", insert metallized nylon and/or insulation material forming an open pocket for the containment of heating pads, and the upper opening 36 and interior or open pocket 38 thereof. The two layers 32 and 34 are secured together along their mutual lower edges 12 and along the extensions 18 and 20. e.g., by stitching 40 as shown in FIG. 2, but are left open along the upper edge 14 for access to the interior or pocket 38, as noted above. Each of the upper edges includes cooperating means for closeably securing the upper edges together, e.g., first and second hook and loop fastening material strips 42 and 44, respective secured thereto. Preferably, hook and loop material 42 and 44 is disposed continually along the upper edges 36 of the first and second layers 32 and 34, in order to provide a continuous seal when closed.

FIGS. 4 and 5 disclose a heating pad cover 50 of similar construction to that of the heating pad 10 of FIGS. 1 through 3, but having a different shape in order to conform closely to the shoulder and upper back areas of a patient. Pad cover 50 includes stitched or otherwise secured together first and second layers, as in cover 10 of the first embodiment, with openable sides (such as the upper back side 52) into which heating and/or moisturized pads may be inserted, in the manner of pad cover 10 of the first embodiment. One or more openable sides may be secured by means of mating hook and loop fastening material, in the manner of pad cover 10. However, the pad cover 50 of FIGS. 4 and 5 has a different planform, in order to conform better to the area of intended use.

Pad cover 50 is defined by a generally vertical edge 54 which lies adjacent the thoracic spine from the end of the neck (cervical 7th vertebra) to the thoracic 10th vertebra when applied to a patient, which edge 54 extends downward to a base edge 56 which extends around the patient's upper waist or mid-lateral area. Edge 56 joins to another axillary edge 58 which lies above the side of the patient when applied, and extends upward to a point beneath the arm. A rear shoulder edge 60 extends upward and outward to provide a relatively wide area extending from the upper spine across the back to wrap around the upper shoulder and rotator cuff area. The rear shoulder edge 60 continues to an upper arm extension 62 and shoulder extension 64, which extensions 62 and 64 are separated by a fold line 66, providing for the folding of extensions 62 and 64 over the shoulder and upper arm in order to provide nearly complete coverage of the shoulder and rotator cuff insertion areas. Shoulder extension 64 joins with the upper edge 52 to complete the periphery of pad cover 50.

Pad cover 50 may be secured about the patient by means of cooperating first and second lower straps 68 and 70, respectively, which join together by means of e.g., mating first and second hook and loop fastener areas 72 and 74 or other suitable means. The upper portion of the pad cover 50 secures about the patient's shoulder by means of a cooperating upper arm extension strap 76 and shoulder extension strap 78 and mating securing means such as hook and loop fastener pads 80, 82. Further security is provided by a second upper arm extension strap 84 and fastening means 86, which extends from the upper arm extension 62 so as to meet with and attach to an upper lateral attachment tab and fastening means 88. The above described construction will be seen to fit closely about one side of the back, side, upper arm, and shoulder of a patient, as shown in FIG. 4, thereby providing close application of heat and/or moisture for treatment.

FIGS. 6 and 7 disclose lower waist and hip pad cover 100 comprising a third embodiment of the present invention. Waist/hip pad cover 100 is constructed in the same manner as the pad covers 10 and 50 of the first two embodiments, including first and second layers and one open but sealable edge (preferably the upper edge 102), with the other edges being permanently secured together. Pad cover 100 is defined by a generally vertical spinal edge 104, extending downward from the upper edge 102 (at the thoracic 10th vertebra) along and below the lower spine of a patient when in use, which vertical edge 104 joins a generally horizontal thigh edge 106 which wraps about the upper thigh of a patient when in use. A curved lateral-frontal edge 108 extends generally upward to connect the thigh edge 106 with the upper edge 102. The thigh edge 106 will be seen to be longer than the upper edge 102, with the curved lateral-frontal edge 108 providing a relatively wider hip coverage area 110 than the waist coverage area 112. This provides a better fit around the typically wider hip structure of the patient for more effective treatment. Waist/hip pad cover 100 is secured about a patient by means of first and second cooperating upper or waist straps 114 and 116, respectively and respective first and second mating upper strap fastening means 118 and 120, and first and second cooperating lower or hip straps 122 and 124, respectively and respective cooperating lower strap fastening means 126 and 128.

The covers 10, 50 and 100 described above may be used to contain virtually any suitable heating pad material (e.g., towels, etc.) but are configured to conform closely to specific areas of the body. Accordingly, specifically configured heating pads have been developed for use in each of the above discussed heating pad covers 10, 50 and 100.

FIG. 8 discloses a cervical heating pad 200 shaped to conform to the interior of the cervical heating pad cover 10 of FIGS. 1 through 3 discussed above. Specifically, cervical heating pad 200 includes a lower edge 202 having a convex curvature, in order to drape downward across the lower cervical vertebrae to a better extent, and yet has a straight upper edge 204 to provide higher coverage across the back of the neck, about the occipital ridge from the mastoid process on the left to the same on the right. The resulting wider central portion 206 provides greater area for more effective treatment.

Left and right frontal neck extensions 208 and 210 of pad 200 extend respectively from the left and right ends of the central area 206, to provide a frontal drape for the pad 200 of FIG. 8. Accordingly, pad 200 will be seen to conform closely with the configuration of the cervical area heating pad cover 10 of FIGS. 1 through 3 discussed above, and is formed to fit closely within the interior space or pocket 38 therein.

Cervical heating pad 200 is constructed of a plurality of generally parallel and substantially tubular enclosures 212, which absorb heat during the heating or warming process and dissipate that heat over a period of time. The outer layers of pad 200 may be formed of a moisture impervious material, although this is not vital to the function of such a pad 200 due to its enclosure in a pad cover 10 or the like for use. The other pads discussed below are constructed in a like manner to that of cervical heating pad 200.

FIG. 9 discloses a heating pad 250 of similar construction to that of the cervical area heating pad 200 of FIG. 8, but having a different shape in order to conform closely to the shoulder, upper back and thoracic areas of a patient. Pad 250 is defined by a generally vertical edge 254 which lies adjacent the thoracic spine from the end of the neck (cervical 7th vertebra) to the thoracic 10th vertebra when applied to a patient, which edge 254 extends downward to a base edge 256 which extends around the patient's upper waist or mid-lateral area. Edge 256 joins another axillary edge 258 which lies above the side of the patient when applied, and extends upward to a point beneath the arm. A rear shoulder edge 260 extends upward and outward to provide a relatively wide area extending from the upper spine across the back to wrap around the upper shoulder and rotator cuff area. The rear shoulder edge 260 continues to an upper arm extension 262 and shoulder extension 264, which extensions 262 and 264 are separated by a fold line 266, providing for the folding of extensions 262 and 264 over the shoulder and upper arm in order to provide nearly complete coverage of the shoulder and rotator cuff insertion areas. Shoulder extension 264 joins with the upper edge 252 to complete the periphery of shoulder pad 250.

The above construction will be seen to provide a pad with congruent shape to that of the shoulder and thoracic pad cover 50 discussed above, but sized so as to be capable of fitting within the pad cover 50. The pad 250 is constructed in the same manner as the construction described for the cervical heating pad 200 of FIG. 8, i. e., being constructed of a plurality of generally parallel and substantially tubular enclosures 268, which absorb heat during the heating or warming process and dissipate that heat over a period of time.

FIG. 10 discloses a lower waist and hip pad 300 comprising an additional embodiment of the present invention. Waist/hip pad 300 is constructed in the same manner as the cervical and thoracic pads 200 and 250 of the other pad embodiments, but is constructed to conform to the interior pocket (not shown) of the lower waist and hip cover 100 of FIG. 7. Pad 300 is defined by a generally vertical spinal edge 304, extending downward from the upper edge 302 (at the thoracic 10th vertebra) along and below the lower buttocks of a patient when in use, which vertical edge 304 joins a Generally horizontal thigh edge 306 which wraps about the upper thigh of a patient when in use. A curved lateral-frontal edge 308 extends generally upward to connect the thigh edge 306 with the upper edge 302. The thigh edge 306 will be seen to be longer than the upper edge 302, with the curved lateral-frontal edge 308 providing a relatively wider hip coverage area 310 than the waist coverage area 312. This provides a better fit around the typically wider hip structure of the patient for more effective treatment. As in the pads 200 and 250 discussed above, waist/hip pad 300 is constructed of a plurality of generally parallel and substantially tubular enclosures 314, which absorb heat during the heating or warming process and dissipate that heat over a period of time. The outer layers of pad 300 may also be formed of a moisture or liquid impervious material as in the case of heating pads 200 and 250 discussed above.

The above described embodiments will be seen to provide relatively complete coverage of commonly afflicted areas and joints of a person's body for heat and/or moisture treatment, with the lower edge 12 of the cervical cover 10 being able to lie substantially adjacent to the upper edge 52 of a shoulder/upper back pad cover 50, and the base or lower edge 56 of such a shoulder/upper back pad cover 50 being disposed substantially adjacent to the upper or waist edge 102 of a waist/hip pad cover 100 when all of the three embodiments 10, 50 and 100 are installed upon a single patient. The various pad covers 10, 50 and 100 provide for the containment of heated and/or moist towels or pads 200, 250 and 300 therein, thereby forming heating pad and cover assemblies and providing transfer of the heat to the patient without passage of the moisture or liquid and resulting evaporation and rapid cooling of the towels or pads. The non-absorbent and moisture repellent material of the covers 10, 50 and 100 provide for relatively easy cleanup of medication and/or contamination from the patient or towels/pads, e. g., by means a wipe down with a disposable germicidal cloth. Thus, a great deal of time, effort and cost may be saved in therapeutic treatment with the present invention, by eliminating the need for frequent exchanges of heated and/or moist towels or pads in the treatment of patients, and the subsequent frequent requirement for the laundering and/or sterilization of such towels and pads. It will further be seen that the covers of the present invention are reversible, with either the first or second sides capable of being placed adjacent the patient to provide for left and right side use as desired and/or required. The present covers may be made in a variety of sizes in order to accommodate various sizes and ages of patients, from small children through large adults.

It is to be understood that the present invention is not limited to the sole embodiments described above, but encompasses any and all embodiments within the scope of the following claims.

I claim:

1. A therapeutic heating pad and cover assembly, comprising:
a heating pad comprising a plurality of generally parallel and substantially tubular enclosures, with said enclosures having means for absorbing heat and releasing heat over a period of time;
a cover comprising a first layer and a second layer each layer composed of a liquid impervious, non-absorbent, flexible fabric material and a contiguous aluminized fabric, said first layer and said second layer having a plurality of sides with at least one side being openable and the remaining sides being permanently secured together therealong, thereby forming a pocket between said first layer and said second layer;
means for closing said openable side;
first and second cooperating attachment straps extending from said remaining sides, with each of said straps respectively having a distal end thereon, whereby;
said openable side is opened, said heating pad is placed within said pocket, said openable side is closed by said a means for closing said openable side, and said cover is secured about a portion of the anatomy of a patient by said first and second cooperating attachment straps to provide heat therapy for the patient and to preclude soiling of the pad and subsequent requirement for frequent cleaning of the pad.

2. The assembly of claim 1 wherein:
said means for closing said openable side of said cover is provided continually along said openable side, thereby providing a continuous seal of said openable side of said cover when said means for closing is closed.

3. The assembly of claim 1 wherein:
said means for closing said openable side of said cover and said first and second cooperating attachment straps include hook and loop material.

4. The assembly of claim 1 wherein:
said liquid impervious, non-absorbent flexible fabric material said cover comprises a synthetic fabric.

5. The assembly of claim 1 wherein:
said first layer and said second layer of said cover are secured together by stitching.

6. The assembly of claim 1 wherein:
said pad and said cover each include a lower side having a convex curvature, an opposite straight upper side with a central area therebetween, and opposite first and second ends respectively having first and second extensions extending therefrom;
said first cooperating attachment strap extending from said first extension, and said second cooperating attachment strap extending from said second extension;
said pad is installed within said cover, said cover is configured to be placed about the back of the neck of a patient with said central area resting thereon and covering the area substantially across the occipital ridge from the left mastoid process to the right mastoid process, with said first and second extensions extending forward and downward over the base of the neck of the patient.

7. The assembly of claim 1 wherein;
said cover includes a substantially horizontal upper side, a substantially vertical spinal side extending downward therefrom, a lower thigh side extending substantially horizontally from said spinal side with said lower thigh side being longer than said upper side, and a lateral and frontal side extending upward from said lower thigh side and curving to join said upper side;
said first and second cooperating attachment straps oppositely extending respectively, from said spinal side and said lateral and frontal side, with each of said attachment straps being displaced upwards from said lower side, and;
first and second cooperating waist straps oppositely extending, respectively, from said spinal side and said lateral and frontal side and adjacent said upper side, whereby;
said pad is installed within said cover, said cover is placed upon a patient with said spinal side substantially aligned with the lower spine of the patient and extending downward substantially from the thoracic tenth vertebra, said first and second cooperating waist straps of said cover are secured together about the waist of the patient, and said first and second cooperating attachment straps of said cover are secured about the lower hips of the patient to secure said pad and said cover about the patient.

8. A therapeutic heating pad and cover assembly comprising a heating pad and a cover, said cover consisting essentially of:
a cover including a first layer and a second layer each layers composed of a non-absorbent flexible fabric material and a contiguous aluminized fabric, said first layer and said second layer having a plurality of sides with at least one side being openable and the remaining said sides being secured together therealong, thereby forming a pocket between said first layer and said second layer;
means for closing said openable side;
said cover further including an area defined by:
a first side having a first upper side end, a second lower side end and a first side length;
a second side having a second upper side end, a second lower side end and a second side length shorter than said first side length; wherein said second side is substantially parallel to said first side;
a lower horizontal side intersecting said first lower side end and said second lower side end;
an upper arm extension having a substantially linear side extending from said second upper side end at an obtuse angle, said upper arm extension further having a curved upper side intersecting said linear side opposite from said second upper side end;
a shoulder extension having a curvilinear side intersecting said curved upper side and said first upper side end;
a first attachable strap depending horizontally from the intersection of said lower horizontal side and said first side;
a second attachable strap depending horizontally from the intersection of said lower horizontal side and said second side;
means for fastening said first and second attachable straps together;
third and fourth attachable straps depending from the intersection of said curved upper side and said linear side;
means for fastening said third and fourth attachable straps together;
a fifth attachable strap depending from said curvilinear side;
a sixth attachable strap depending from the intersection of said linear side and said second side; and means for fastening said fifth and sixth attachable straps together.

9. The assembly of claim 1 wherein said cover further includes an area defined by;
   a first side having a first upper side end, a second lower side end and a first side length;
   a second side having a second upper side end, a second lower side end and a second side length shorter than said first side length; wherein said second side is substantially parallel to said first side;
   a lower horizontal side intersecting said first lower side end and said second lower side end;
   an upper arm extension having a substantially linear side extending from said second upper side end at an obtuse angle, said upper arm extension further having a curved upper side intersecting said linear side opposite from said second upper side end;
   a shoulder extension having a curvilinear side intersecting said curved upper side and said first upper side end;
   a first attachable strap depending horizontally from the intersection of said lower horizontal side and said first side;
   a second attachable strap depending horizontally from the intersection of said lower horizontal side and said second side;
   means for fastening said first and second attachable straps together;
   third and fourth attachable straps depending from the intersection of said curved upper side and said linear side;
   means for fastening said third and fourth attachable straps together;
   a fifth attachable strap depending from said curvilinear side;
   a sixth attachable strap depending from the intersection of said linear side and said second side; and
   means for fastening said fifth and sixth attachable straps together.

10. A therapeutic heating pad and cover assembly comprising a heating pad and a cover, said cover consisting essentially of:
   a cover including a first layer and a second layer, each layer composed of a non-absorbent flexible fabric material and a contiguous of aluminized fabric, said first layer and said second layer having a plurality of sides with at least one side being openable and the remaining said sides being secured together therealong, thereby forming a pocket between said first layer and said second layer;
   means for closing said openable side;
   said cover further including an area defined by:
      a first side having an upper first side end and a lower second side end;
      a second side having a upper second side end and a curved lower second side end; wherein said second side is substantially parallel to said first side;
      a lower horizontal side intersecting said lower first side end and said curved lower second side end;
      an upper horizontal side intersecting said upper first side end and said upper second side end;
   a first attachable strap depending horizontally from said lower first side;
   a second attachable strap depending horizontally from said curved lower second side;
   means for fastening said first and second attachable straps together;
   a third attachable strap depending from the intersection of said upper first side and said upper horizontal side;
   a fourth attachable strap depending from the intersection of said upper second side and said upper horizontal side;
   means for fastening said third and fourth attachable straps together.

* * * * *